(12) United States Patent
Kawashima

(10) Patent No.: US 9,422,588 B2
(45) Date of Patent: *Aug. 23, 2016

(54) BACTERIA MEASURING APPARATUSES

(71) Applicant: Sysmex Corporation, Kobe (JP)

(72) Inventor: Yasuyuki Kawashima, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 284 days.

This patent is subject to a terminal disclaimer.

(21) Appl. No.: 14/151,033

(22) Filed: Jan. 9, 2014

(65) Prior Publication Data

US 2014/0127794 A1   May 8, 2014

Related U.S. Application Data

(63) Continuation of application No. 10/821,732, filed on Apr. 8, 2004, now Pat. No. 8,669,097.

(30) Foreign Application Priority Data

Apr. 10, 2003 (JP) ................................. 2003-106569

(51) Int. Cl.

| | |
|---|---|
| *C12Q 1/04* | (2006.01) |
| *C12Q 1/18* | (2006.01) |
| *G01N 33/569* | (2006.01) |
| *G01N 33/573* | (2006.01) |
| *C12Q 1/14* | (2006.01) |
| *C12Q 1/10* | (2006.01) |
| C12N 9/24 | (2006.01) |
| G01N 15/14 | (2006.01) |

(52) U.S. Cl.
CPC .. *C12Q 1/14* (2013.01); *C12Q 1/04* (2013.01); *C12Q 1/10* (2013.01); *G01N 15/1459* (2013.01); *G01N 2015/1402* (2013.01)

(58) Field of Classification Search
USPC .......................... 435/29, 34, 261, 32, 6.12, 80
IPC ..... C12N 9/24; C12Q 1/04,1/18; G01N 33/569, G01N 33/573
See application file for complete search history.

(56) References Cited

U.S. PATENT DOCUMENTS

| | | | |
|---|---|---|---|
| 5,631,165 A | 5/1997 | Chupp et al. | |
| 5,821,127 A | 10/1998 | Akai et al. | |
| 6,004,816 A | 12/1999 | Mizukami et al. | |
| 6,165,740 A | 12/2000 | Fukuda et al. | |
| 7,632,683 B2 * | 12/2009 | Kawashima et al. | 436/63 |
| 8,153,418 B2 * | 4/2012 | Kawashima | 435/288.7 |
| 8,669,097 B2 * | 3/2014 | Kawashima | 435/283.1 |

FOREIGN PATENT DOCUMENTS

| | | |
|---|---|---|
| EP | 1 136 563 A2 | 9/2001 |
| EP | 1 203 825 A2 | 5/2002 |
| JP | 2001-140091 | 6/2001 |
| JP | 2001-258590 | 9/2001 |

OTHER PUBLICATIONS

B-D FACStar Plus Cell Sorter Flow Cytometer at http://www.biomedika.com Tue Apr. 23 16:51:45 EST 2002, Printed May 27, 2010.
Dow et al. 1979, Particle size distribution analysis for the rapid detection of microbial infection of urine. Journal of Clinic Pathology, vol. 32, pp. 386-390.
Ito, K.; Tatsumi, N.; Kikuchi, H.; Takahashi, F.; Koba, T.; Nozaki, T.; Ando, Y. "Basic Evaluation of the New Fully Automated Urine Sediment Analyzer (U-FCM) Based on Flowcytometric Technology,"Japan Journal of Clinical Pathology, 1994, 42, pp. 1093-1098.
Kubitschek HE et al (Dec. 1986) Determination of bacterial cell volume with the Coulter Counter. J Bacteriol, vol. 168, No. 3, pp. 1466-1467.
Pinder, A.C.; Purdy, P.W.; Poulter, S.A.G.; Clark, D.C. "Validation of Flow Cytometry for Rapid Enumeration of Bacterial Concentrations in Pure Cultures,"Journal of Applied Bacteriology, 1990, 69, pp. 92-100.
Walner, G.; Fuchs, B.; Spring, S.; Beisker, W.; Amann, R. "Flow Sorting of Microorganisms for Molecular Analysis," Appl. Environ. Microbiol., 1997, pp. 4223-4231.

* cited by examiner

*Primary Examiner* — Debbie K Ware
*Assistant Examiner* — Kailash C Srivastava
(74) *Attorney, Agent, or Firm* — Brinks Gilson & Lione

(57) ABSTRACT

An apparatus for measuring bacteria includes a sampling device for processing fluorescently stained bacteria, a detector for detecting size information from the bacteria in the sample, and a detector for detecting fluorescence information expressing intensity of fluorescent light emitted by the bacteria. The apparatus further includes a processor and memory that includes programs for creating a scattergram representing a distribution of the bacteria based on the size information and the fluorescence information detected, analyzing the distribution of the bacteria in the scattergram, and determining whether the bacteria in the sample is *bacillus* or *coccus* based on a result of the analysis.

15 Claims, 13 Drawing Sheets

BACTERIA MEASURING APPARATUSES

RELATED APPLICATIONS

This application is a continuation application of U.S. patent application. Ser. No. 10/821,732, filed Apr. 8, 2004, now U.S. Pat. No. 8,669,097, which claims priority under 35 U.S.C. §119 to Japanese Pat. Appl. No. 2003-106569, filed Apr. 10, 2003, the entire contents of which are incorporated by reference herein.

FIELD OF THE INVENTION

The present invention relates to apparatuses, methods, and programs for automatically detecting bacteria in a sample and, more particularly, to apparatuses, methods, and programs for automatically detecting a *bacillus* or *coccus* bacterium in a sample.

BACKGROUND

Detection of bacteria contained in a sample and determination of the type of bacteria are often performed in clinical examinations and food sanitation examinations. The types of bacteria are typically classified by Gram stainability of the bacteria (e.g., Gram positive or Gram negative), and by shape (e.g., *bacillus* or *coccus*). Gram-negative *bacillus* and Gram-positive *coccus* frequently produce adverse effects on the human body.

The agar culture method is the most common method for classifying bacteria. This method involves culturing a sample in an agar medium for a predetermined time, either staining or not staining colonies formed in the culture, and having an observer classify the bacteria using a microscope. However, the agar culture method is a difficult process inasmuch as it is essentially a manual method. Furthermore, considerable time must elapse before the type of bacterium can be determined since culturing is required.

In recent years, methods have been tried which automatically measure bacteria using a particle analyzer, such as a flow cytometer or the like. This technology involves the following aspects: (1) a method and apparatus for measuring microorganisms, which respectively measure pre-culture and post-culture samples to prevent measurement errors due to impurities in the sample by determining the difference between the two measurement results (e.g., see: U.S. Pat. No. 6,165,740); and (2) a method for counting bacteria in samples containing impurities, which separates the bacteria from the impurities, counts the bacteria by adding a cationic surfactant to a sample containing bacteria so as to increase the colorant transmission of the bacteria, and stains the bacteria through the action of the colorant (e.g., see: European Patent Publication No. 1136563 A2).

Measurement can be accomplished in a relatively short time when the method automatically measures the bacteria by a particle measuring apparatus such as a flow cytometer or the like. However, among such methods, no technique has yet been proposed for differentiating *bacillus* and *coccus* with greater accuracy.

SUMMARY

The scope of the present invention is defined solely by the appended claims, and is not affected to any degree by the statements within this summary.

A method for measuring bacteria embodying features of the present invention includes (a) fluorescently staining bacteria in a sample; (b) detecting size information from the bacteria in the sample, and fluorescence information expressing intensity of fluorescent light emitted by the bacteria; (c) creating a scattergram representing a distribution of the bacteria based on the size information and the fluorescence information detected; (d) analyzing the distribution of the bacteria in the scattergram; and (e) determining whether the bacteria in the sample is *bacillus* or *coccus* based on a result of the analyzing.

A bacteria measuring apparatus embodying features of the present invention includes: (a) a sampling device for sampling a sample containing fluorescently stained bacteria; (b) a first detector for detecting size information from each bacterium in the sample; (c) a second detector for detecting fluorescence information expressing intensity of fluorescent light emitted from each bacterium in the sample; and (d) a control unit configured for creating a scattergram of the bacteria using the size information and the fluorescence information as parameters, for analyzing distribution of the bacteria in the scattergram, and for determining whether the bacteria in the sample is *bacillus* or *coccus* based on an analysis result.

A computer-executable program for analyzing bacteria embodying features of the present invention includes: (a) obtaining size information of bacteria and fluorescence information expressing intensity of fluorescent light emitted by the bacteria; (b) creating a scattergram representing a distribution of the bacteria based on the size information and the fluorescence information; (c) analyzing the distribution of the bacteria in the scattergram; and (d) determining whether the bacteria is *bacillus* or *coccus* based on a result of the analyzing.

DETAILED DESCRIPTION

Figure 1:
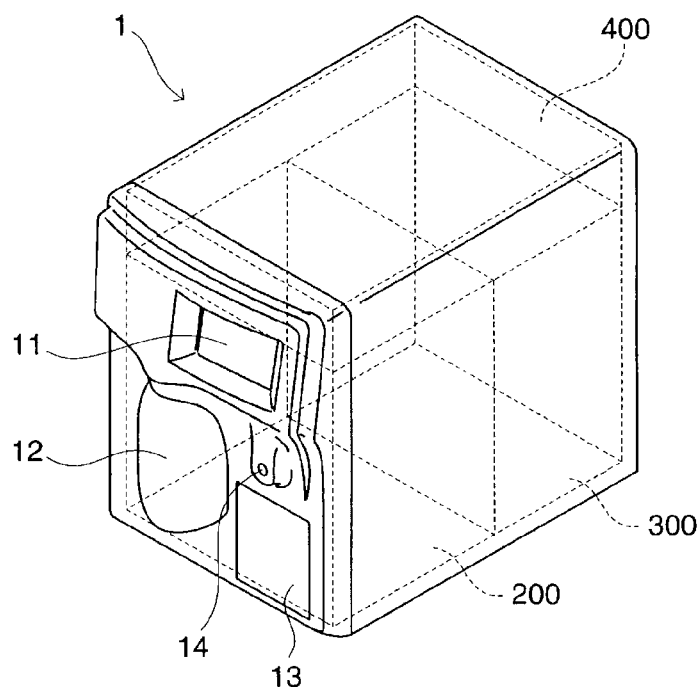
FIG. 1 is a perspective view of an automated bacteria measuring apparatus embodying features of the present invention.

The present invention provides techniques, apparatuses, and computer readable programs for rapidly and accurately determining whether the type of bacteria in a sample is *bacillus* or *coccus*.

The methods for measuring bacteria in accordance with the present invention include (a) preparing a sample by fluorescently staining the bacteria in a specimen; (b) detecting size information of the bacteria and fluorescence information expressing the intensity of fluorescent light emitted by the bacteria of each type in a prepared sample; (c) creating a scattergram using the detected size information and fluorescence information as parameters; (d) analyzing the distribution of the bacteria in the scattergram; and (e) determining whether the type of bacteria in the sample is *bacillus* or *coccus* based on the analysis result.

A fluorescent dye for bonding to components of the bacteria and emitting fluorescent light is used in the bacteria fluorescent stain. For example, bacteria in a specimen may be uniquely stained using a nucleic acid staining dye which uniquely bonds with intracellular DNA and RNA of the bacteria. By way of example, polymethene dyes having structures (1) through (11) below may be used:

(1) Thizole orange (2)

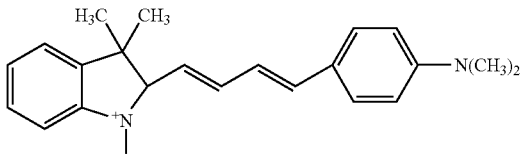

(3)

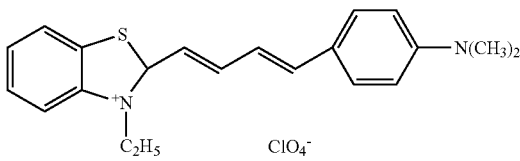

(4)

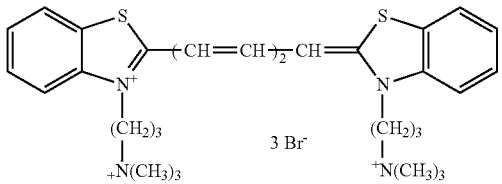

(5)

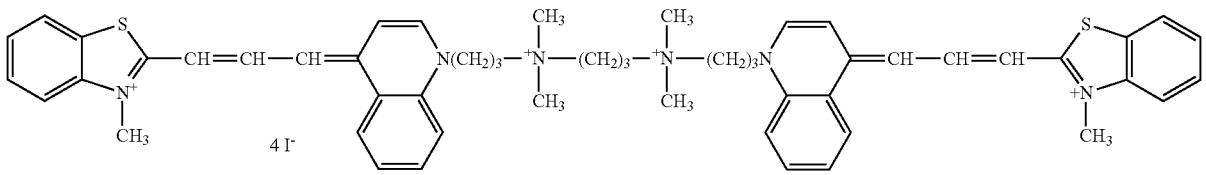

(6)

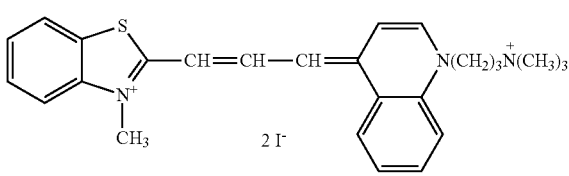

(7)
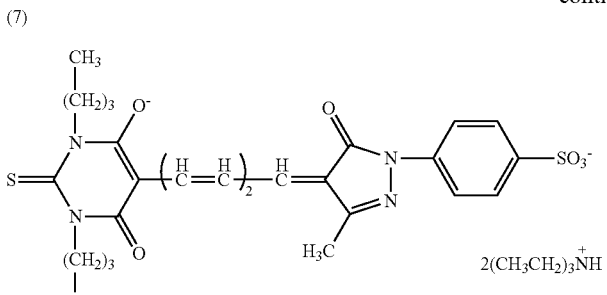

(8)
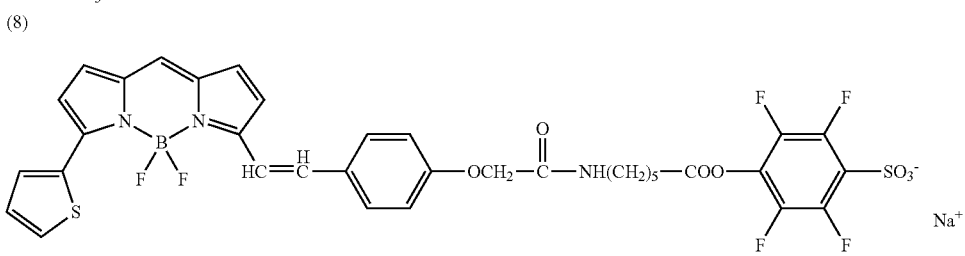

(9)
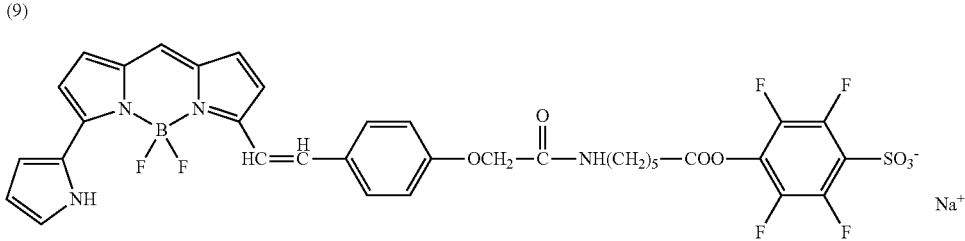

(10) Compounds having the general formula:

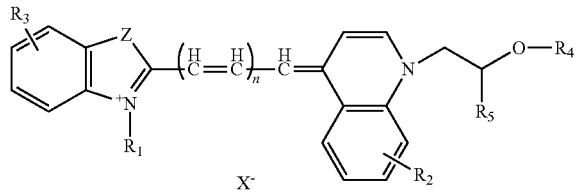

wherein, $R_1$ represents a hydrogen atom or an alkyl group having 1 to 3 carbon atoms; $R_2$ and $R_3$ represent hydrogen atoms, alkyl groups having 1 to 3 carbon atoms, or alkoxy groups having 1 to 3 carbon atoms; $R_4$ represents a hydrogen atom, acyl group, or alkyl group having 1 to 3 carbon atoms; $R_5$ represents a hydrogen atom or alkyl group having 1 to 3 carbons atoms which may optionally be substituted; Z represents a sulfur atom, oxygen atom or carbon atom substituted by two alkyl groups having 1 to 3 carbon atoms; n represents 1 or 2; and X represents an anion.

(11) Compounds having the general formula:

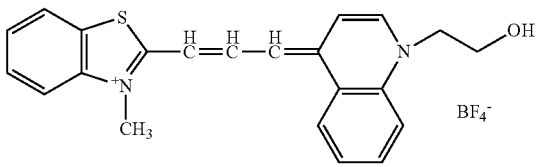

wherein, $R_6$ represents a hydrogen atom or alkyl group having 1 to 18 carbon atoms; $R_2$ and $R_8$ represent hydrogen atoms, alkyl groups having 1 to 3 carbon atoms, or alkoxy groups having 1 to 3 carbon atoms; $R_9$ represents a hydrogen atom, acyl group, or alkyl group having 1 to 18 carbon atoms; Z represents a sulfur atom, oxygen atom or carbon atom substituted by two alkyl groups having 1 to 3 carbon atoms; n represents 0, 1, or 2; and X represents an anion.

Among these dyes, (1) is commercially available, (2) and (3) are available from Japan Photosensitive Dye Research Center, and (5) through (9) are available from Molecular Probes, Inc. Dye (10) may be manufactured by the method described in U.S. Pat. No. 5,821,127. Dye (11) may be manufactured by the method described in U.S. Pat. No. 6,004,816.

Among the dyes represented by the general formula (10), the dye shown below is particularly desirable at present:

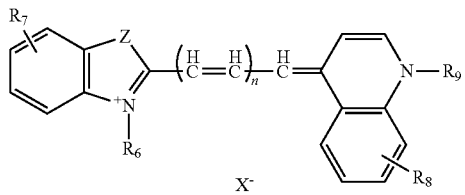

Bacteria having a specific level of fluorescent intensity may be distinguished from impurities which substantially lack fluorescent intensity if fluorescent information (fluorescent intensity) is detected from each particle in a sample subjected to a fluorescent staining process using the above-mentioned fluorescent dyes.

Electrical resistance methods, which use a detector having a member comprising a pore for passing through bacteria and first and second electrodes, detect the size of particles from the change in electrical resistance of a sample over time when the prepared sample passes through the pore. These methods may be used for detecting particle size information. Methods which detect scattered light pulse width or scattered light intensity emitted by particles using flow cytometry may also be used for detecting particle size information. In these methods, particle size information includes information reflecting particle diameter, particle width in a direction perpendicular to the particle diameter, particle volume or the like. The value of the change in electrical resistance detected by the electrical resistance method, and the pulse width and intensity of the scattered light signal detected by the flow cytometry method may be used as the size information.

Methods for detecting the intensity of fluorescent light emitted by fluorescently stained particles via flow cytometry may be used as the method for detecting fluorescence information.

Flow cytometry is a method in which laser light is used to irradiate a flowing sample fluid which contains target particles such as bacteria and cells. Optical information concerning scattered light and fluorescent light generated when the particles pass through the laser irradiation area is detected. Subsequently, the particles are analyzed based on the detected optical information. The various optical information is detected as pulse-like electrical signals by photoelectric conversion elements, such as photodiodes, photomultiplier tubes, and the like. Using these signals, signal intensity may be obtained based on the pulse peak height, and the light emission time may be obtained based on the pulse width. In general, the forward scattered light signal reflects the size of the particle, and the fluorescent light signal reflects the degree of staining of the particle which was fluorescently stained beforehand.

A scattergram is composed of dots corresponding to individual particles based on a plurality of particle information detected from each particle on a coordinate space having as its axes a plurality of types of information (e.g., size information expressing the size of the particle, and fluorescent light information), which reflect the characteristics of the particle. When the particle properties differ, differences occur in the distribution of dots on the scattergram. The present inventors have discovered that when *bacillus*-containing samples and *coccus*-containing samples were compared, the size information of both are substantially identical but the obtained fluorescent light information tends to be greater for the *bacillus* than for the *coccus*, which results in differences in the dot distribution on the scattergram. Thus, in accordance with the present invention, a determination as to whether bacteria in a sample is *bacillus* or *coccus* is based on the differences in this distribution.

Figure 7:
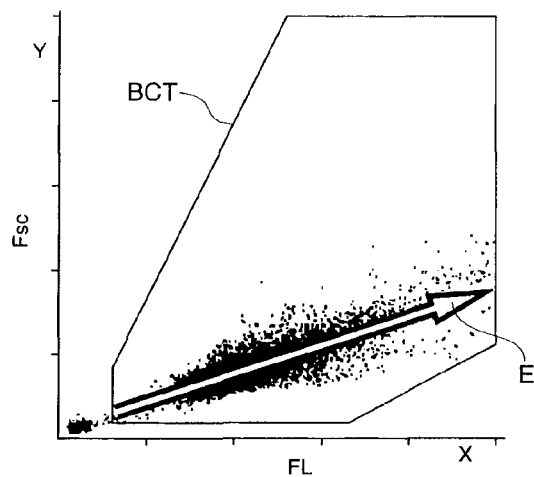
FIG. 7 shows an example of a scattergram prepared by an automated bacteria measuring apparatus embodying features of the present invention.
Figure 8:
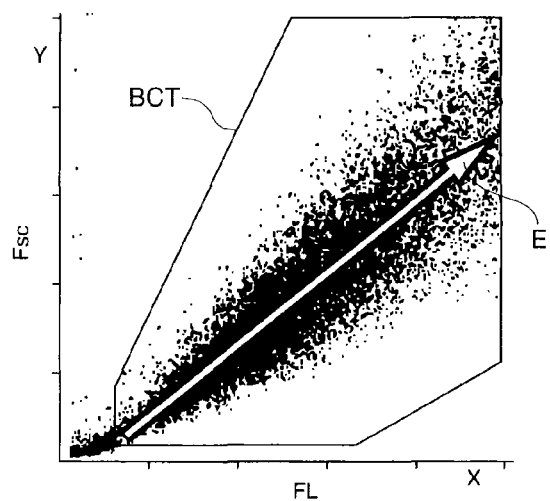
FIG. 8 shows an example of a scattergram prepared by an automated bacteria measuring apparatus embodying features of the present invention.

Differences in the distribution of dots in a *bacillus* specimen and *coccus* specimen are expressed in the slopes of the distributions. The slopes of the distributions are described below. FIG. 7 shows an example of a scattergram obtained from a specimen containing *bacillus*, and FIG. 8 shows an example of a scattergram obtained from a specimen containing *coccus*, wherein the fluorescent intensity (FL) is plotted on the X axis, and the forward scattered light intensity (Fsc) is plotted on the Y axis. Region BCT in the drawings is regarded as the region in which dots corresponding to bacteria appear. The population of dots corresponding to bacteria in the scattergrams is distributed so as to extend in a fixed direction (from lower left to upper right). In the coordinate space of the scattergrams, the slope having this "fixed direction" is the slope of the distribution. When FIGS. 7 and 8 are compared, the slope relative to the X axis in the direction in which the population extends to the upper right (i.e., slope of the distribution) is larger in the *coccus*-containing specimen (FIG. 8) than in the *bacillus*-containing specimen (FIG. 7). From this fact, in accordance with the present invention, a determination as to whether bacteria in a specimen is *bacillus* or *coccus* is based on the slope of the distribution. The slope of the distribution is determined in the direction of maximum variance of the dots representing the bacteria, and the slope of the distribution may be determined by determining the slope in the maximum variance direction. A slope of approximate expression calculated from the dots representing the bacteria may also be used as the slope of the distribution.

An embodiment of the automated bacteria measuring apparatus of the present invention is described below. In FIG. 1, an external view of an automated bacteria measuring apparatus 1 is indicated by the solid lines, and the internal structure is briefly indicated by the dashed lines. The foremost surface of the apparatus is provided with an output part (e.g. a liquid crystal touch panel 11 for inputting various types of settings and displaying measurement results), specimen cover 12, reagent cover 13, and start switch 14. When the specimen cover 12 is opened, a specimen may be set in the specimen holding unit provided within the apparatus. When the reagent cover 13 is opened, reagent may be set in the reagent holding unit provided within the apparatus. The specimen holding unit and the reagent holding unit are further described below.

In the internal structure of the apparatus indicated by the dashed lines, the top part accommodates an analysis control unit 400, which includes a microcomputer and various types of circuits, and the like. The bottom part nearest the front side accommodates a sample preparation unit 200 for preparing sample fluids. The bottom part on the back side accommodates a detection unit 300 for detecting signals from the bacteria in the sample fluid.

Sample Preparation Unit

Figure 2:
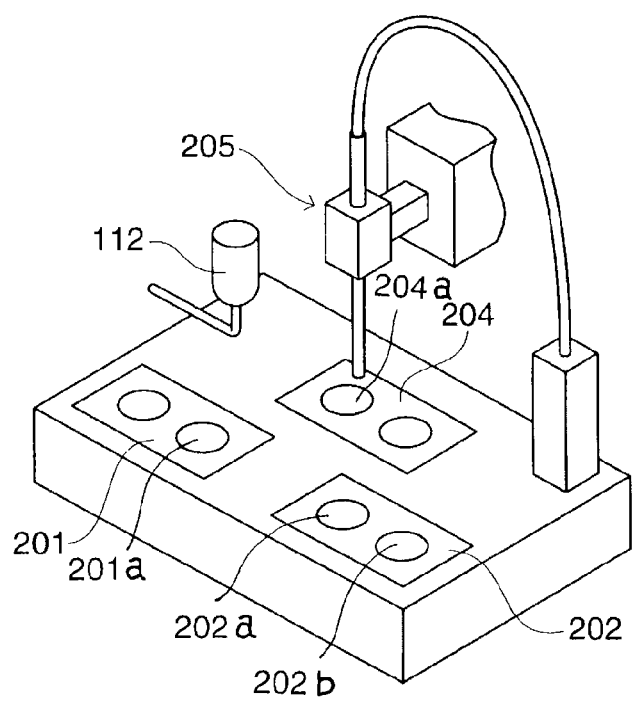
FIG. 2 is a perspective view of the sample preparation unit of an automated bacteria measuring apparatus embodying features of the present invention.

FIG. 2 shows the sample preparation unit 200 of the automated bacteria measuring apparatus 1. The sample preparation unit 200 is provided with a specimen holding unit 201, reagent holding unit 202, incubator 204 as a reaction unit, and dispenser 205. A receptacle 201*a* for accepting a specimen is placed in the specimen holding unit 201. In the automated bacteria measuring apparatus 1, a dilution fluid and staining fluid are used as measurement reagents, and a receptacle 202*a* accommodating a dilution fluid and a receptacle 202*b* accommodating a staining fluid are respectively set in the reagent holding unit 202. A receptacle 204*a* for reacting the specimen and the reagent is placed in the incubator 204. A dispenser 205 is movable vertically, forward and back, and side to side via a drive device, and suctions and discharges a set amount of fluid. The dispenser 205 respectively suctions predetermined amounts of specimen in the specimen receptacle 201*a* set in the specimen holding unit 201, and dilution fluid in the dilution receptacle 202*a* or staining fluid in the receptacle 202*b* set in the reagent holding unit 202. The dispenser 205 discharges the fluid to the receptacle 204*a* set in the incubator 204. The incubator 204 maintains a predetermined temperature, and reacts the specimen and reagent to prepare a sample. The prepared sample is sampled by the dispenser 205, and supplied to the sample receptacle 112. Details of the operation of the sample preparation unit 200 are further described below.

Detection Unit

Figure 3:
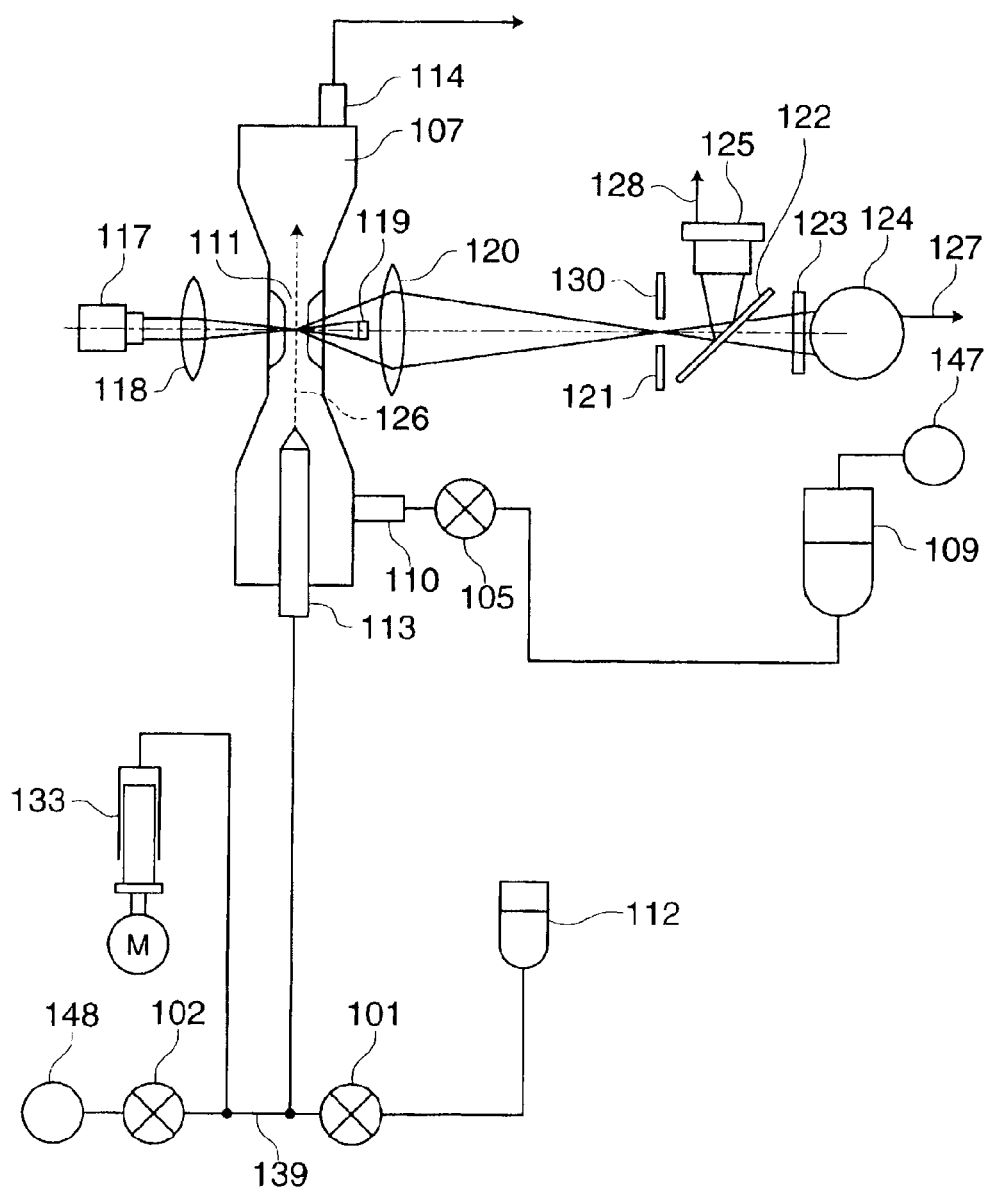
FIG. 3 is an illustration of the optical system and flow system of the detection unit of an automated bacteria measuring apparatus embodying features of the present invention.

FIG. 3 illustrates the optical system and flow system of the detection unit 300. A sheath flow cell 107 is used to flow the sample fluid supplied from the sample receptacle 112 of the sample preparation unit 200, and is connected to the sample receptacle 112. Furthermore, the sheath flow cell 107 is provided with a nozzle 113, which discharges sample fluid toward an orifice 111, a sheath fluid supply port 110, and drainage port 114. Near the sheath flow cell 107 are disposed a laser light source 117 for irradiating a laser beam on a sample fluid flowing in the sheath flow cell 107, and various types of optical components (condenser lens 118, beam stopper 119, collector lens 120, shield plate 130 having a pin-hole 121, dichroic mirror 122, and filter 123) for condensing the fluorescent light and forward scattered light emitted from the particles in the sample fluid irradiated by the laser light. Furthermore, a photomultiplier tube 124 is provided as a detection device for detecting condensed fluorescent light, and a photodiode 125 is provided as a detection device for detecting forward scattered light.

A sheath fluid receptacle 109, which is pressurized by a positive pressure pump 147, is connected to the sheath fluid supply port 110 through a valve 105. The drainage port 114 is connected to a waste fluid chamber (not shown). The nozzle 113 is connected to the sample receptacle 112 through a valve 101, and to a negative pressure pump 148 through a flow path 139 and valve 102. A syringe pump 133 is connected on the valve 102 side of the flow path 139.

The detection unit 300 of the above-described structure detects forward scattered light signals and fluorescent light signals from particles of bacteria and the like included in a sample prepared in the sample preparation unit 200 as it flows through the sheath flow cell 107. The detected signals are transmitted to an analysis control unit 400. Detailed operation of the detection device 300 is described below.

Analysis Control Unit

Figure 4:
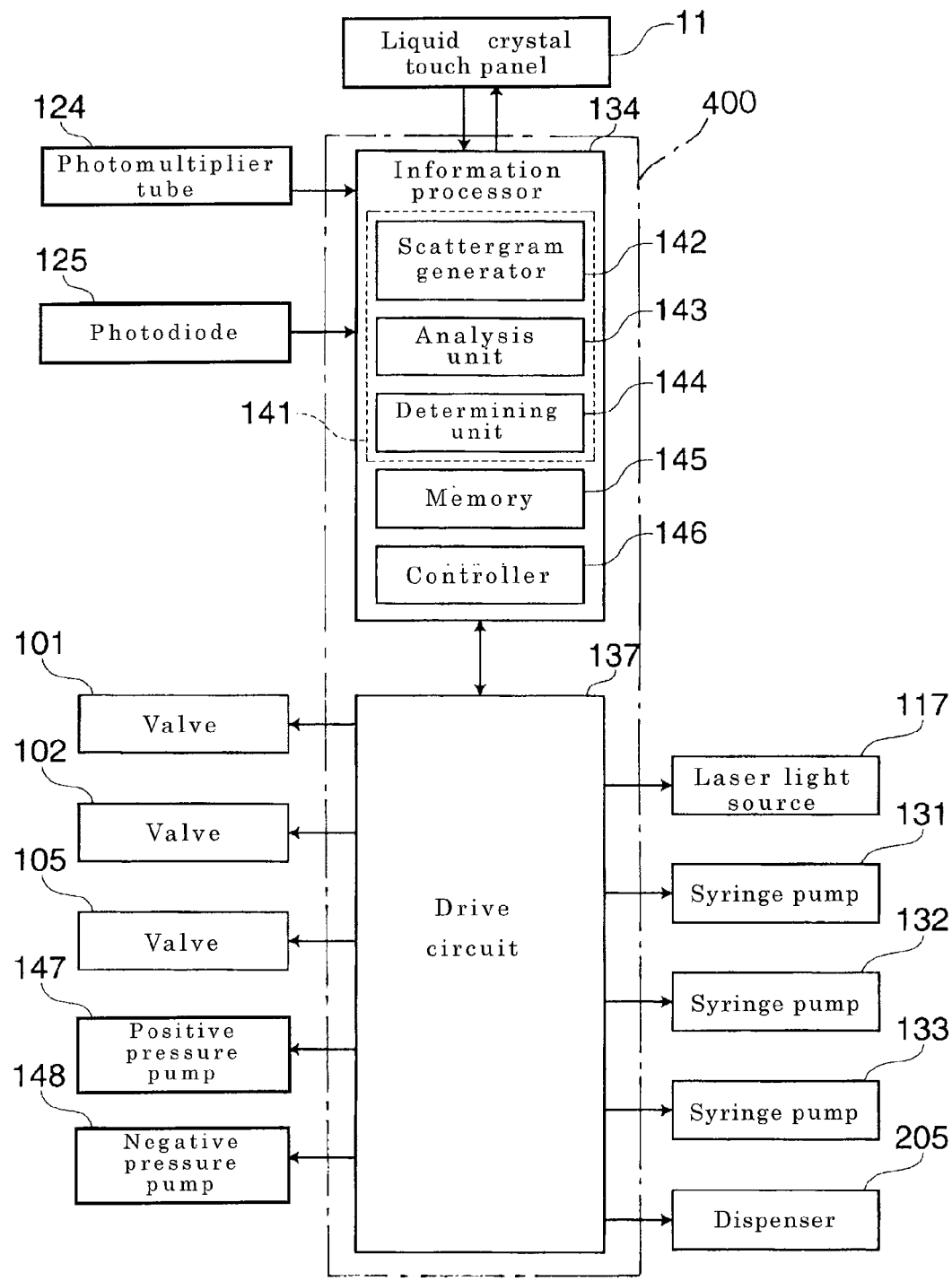
FIG. 4 is a block diagram of the analysis control unit of an automated bacteria measuring apparatus embodying features of the present invention.

FIG. 4 is a block diagram showing the structure of the analysis control unit 400. The analysis control unit 400 includes a computer incorporating a CPU, RAM, ROM, hard disk, and the like, and various types of circuits, and functions as an information processor 134 and a drive circuit 137. As shown in FIG. 4, the information processor 134 is provided with an analyzer 141, memory 145, and controller 146, and the analyzer 141 is provided with a scattergram generator 142, analysis unit 143, and determining unit 144.

The memory 145 stores (a) analysis programs for analyzing, via the analyzer 141, the signals obtained from particles in the sample fluid by the detecting unit 300, and (b) control programs for controlling the operation of each part of the apparatus. The controller 146 controls the drive circuit 137 based on the control program. The drive circuit 137 drives the dispenser 205 shown in FIG. 2, syringe pump 133 shown in FIG. 3, valves 101, 102, 105, positive pressure pump 147, negative pressure pump 148, and laser light source 117 based on the control of the controller 146.

General Controls

Figure 5:
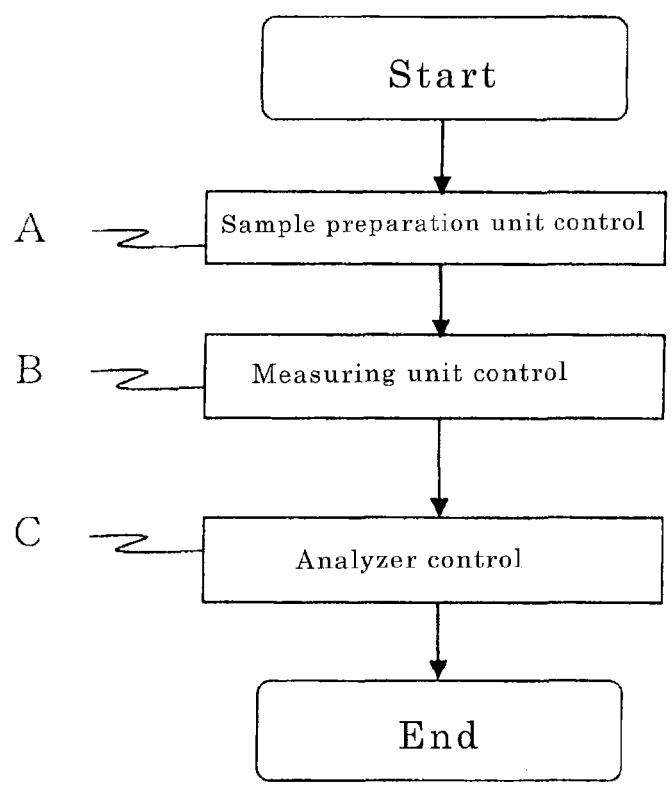
FIG. 5 is a flow chart showing the overall control of an automated bacteria measuring apparatus embodying features of the present invention.

FIG. 5 is a flow chart of the general control of the automated bacteria measuring apparatus 1 accomplished via the control program. After the receptacle 201*a* accommodating a specimen is placed in the specimen holding unit 201, the receptacle 202*a* accommodating a dilution fluid and receptacle 202*b* accommodating a staining fluid are placed in the reagent holding unit 202. The receptacle 204*a* for reacting the specimen and reagent (which is empty at this time) is placed in the incubator 204 of the sample preparation unit 200 (FIG. 2). When the start switch 14 is pressed, the control program starts, and step A (sample preparation unit control), step B (detection unit control), and step C (analyzer control) are sequentially executed. In this way, the sample preparation unit 200, detection unit 300, and analyzer 141 are controlled, and the series of operations of the automated bacteria measuring apparatus 1 are automatically executed. Details of the operation of each part of the apparatus in steps A, B, and C are described below.

Step A Control of the Sample Preparation Unit

The operation of the sample preparation unit 200 by the sample preparation unit control is described below in reference to FIG. 2. First, the dispenser 205 measures a fixed quantity of the bacteria-containing specimen from the receptacle 201*a* of the sample holding unit 201, and dispenses 50 µl into the receptacle 204*a* of the incubator 204. Next, the dispenser 205 measured a fixed quantity of dilution solution from the receptacle 202*a* of the reagent holding unit 202, and dispenses 340 µl into the sample-containing receptacle 204*a*. The incubator 204 mixes the sample and the specimen and the dilution fluid for 10 seconds while maintaining a temperature of 42° C. Then, the dispenser 205 measures a fixed quantity of staining fluid from the receptacle 202*b* of the reagent holding unit 202, and dispenses 10 µl into the receptacle 204*a*. The incubator 204 shakes and mixes the fluids to induce reaction of the staining fluid while maintaining the receptacle 204*a* at 42° C. so as to prepare a sample. Approximately 400 µl of the prepared sample is retrieved by the dispenser 205, and supplied to the sample receptacle 112. The sample in the sample receptacle 112 flows to the sheath flow cell 107 of the detection unit 300, as described below.

Step B (Control of the Detection Unit)

The operation of the detection unit 300 by the detection unit control is described below in reference to FIG. 3. When the sample prepared by the sample preparation unit 200 is accommodated in the sample receptacle 112, the negative pressure pump 148 is actuated. Valves 101 and 102 are simultaneously opened, and the sample fills the flow path 139 between the valves 101 and 102 due to the negative pressure. Thereafter, the valves 101 and 102 are closed.

Next, the syringe pump 133 forces a fixed quantity of the sample in the flow path 139 into the nozzle 113, and the sample is discharged from the nozzle 113 into the sheath flow cell 107. Then, a sheath fluid is supplied from the sheath fluid container 109 to the sheath flow cell 107 by opening the valve 105 simultaneously with the discharge.

In this manner, the sample is surrounded by the sheath fluid, and the flow is constricted by the orifice 111. By constricting the flow of the sample, the particles contained in the sample fluid flow along in a linear alignment. When the sample passes through the orifice 111, the sheath fluid is discharged to the drain port 114.

A laser beam emitted from the laser light source 117 and constricted by the condenser lens 118 irradiates the sample flow 126 flowing through the orifice 111.

The laser light transmitted through the sheath flow cell 107 without irradiating the particles in the sample is blocked by the beam splitter 119. The forward scattered light and fluorescent light emitted from the particles irradiated by the laser beam are condensed by the collector lens 120, and pass through pin hole 121 of the light shield 130. This light then impinges the dichroic mirror 122.

The fluorescent light, which has a longer wavelength than the forward scattered light, is transmitted directly through the dichroic mirror 122, detected by the photomultiplier tube 124 after the forward scattered light has been removed by the filter 123, and output as a fluorescent light signal 127 (a pulse-like electrical signal).

Furthermore, the forward scattered light is reflected by the dichroic mirror 122, received by the photodiode 125, and output as a forward scattered light signal 128 (a pulse-like electrical signal). Then, the fluorescent light signal 127 and the forward scattered light signal 128 are input to an information processor 134 shown in FIG. 4.

Step C Control of the Analyzer

When the fluorescent light signal 127 and forward scattered light signal 128 from the detection unit 300 are input to the information processor 134, the signals are analyzed by the analyzer 141. This forms step C (control of the analyzer) in the general control of the automated bacteria measuring apparatus 1. The operation of the analyzer 141 via the analyzer control is described below in reference to the flow chart of FIG. 6. Although the program representing this operation sequence is stored beforehand in the memory 145 together with other programs, this program also may be supplied from an external memory medium or communication network.

First, the fluorescent light signal 127 and the forward scattered light signal 128 detected by the detection unit 300 are input to the scattergram generator 142 of the analyzer 141 (S1).

The scattergram generator 142 calculates the forward scattered light intensity Fsc from the maximum peak value of the input forward scattered light signal 128 as particle size information. Similarly, the fluorescent light intensity FL is calculated from the fluorescent light signal 127 as fluorescent light information. Then, a two-dimensional scattergram is created by plotting the obtained FL on the X axis, and the Fsc on the Y axis (S2).

The analysis unit 143 discriminates the dots corresponding to bacteria from the dots appearing on the generated two-dimensional scattergram, and counts the particles identified as bacteria (S3). FIG. 7 shows an example of a two-dimensional scattergram generated from a *bacillus* bacteria-containing specimen. As shown in FIG. 7, the region BCT in which the bacteria are focused is set beforehand by discriminating the bacteria from the other particles. In this manner, the particles appearing within the BCT region are regarded as bacteria, and the particles within the region BCT are counted as bacteria.

Figure 9:
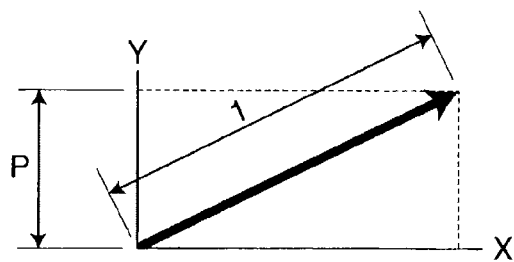
FIG. 9 illustrates the unit vector used in the analysis process performed by an automated bacteria measuring apparatus embodying features of the present invention.

The analysis unit 143 determines the variance of the dots of particles within the BCT region in the X-Y two-dimensional space, and determines the directional vector E in which there is maximum variance through the center of the variance. The determined directional vector E is shown in FIG. 7. The determined directional vector E is then converted to a unit vector (a vector having a length of 1), as shown in FIG. 9. The unit vector is broken down into a component in the X axis direction and a component in the Y axis direction, and the magnitude of the component in the Y axis direction is designated as P (S4). P is a value representing the degree of slope of the directional vector relative to the X axis.

FIG. 8 shows an example of a two-dimensional scattergram generated from a *coccus*-containing specimen, and indicates the determined directional vector similar to FIG. 7. A comparison of FIGS. 7 and 8 clearly shows that the degree of slope of the directional vector relative to the X axis is greater in the *coccus*-containing specimen (FIG. 8) than in the *bacillus*-containing specimen (FIG. 7). Thus, the value of P is also greater in the *coccus*-containing specimen (FIG. 8) than in the *bacillus*-containing specimen (FIG. 7). The determining unit 144 compares the value of P calculated by the analysis unit 143 to a predetermined value A (in this case, A=0.68) (S5). When P≥A, the bacteria included in the specimen is determined to be *coccus* (S6 and S7), whereas when P<A, the bacteria is determined to be *bacillus* (S6 and S8).

Figure 10:
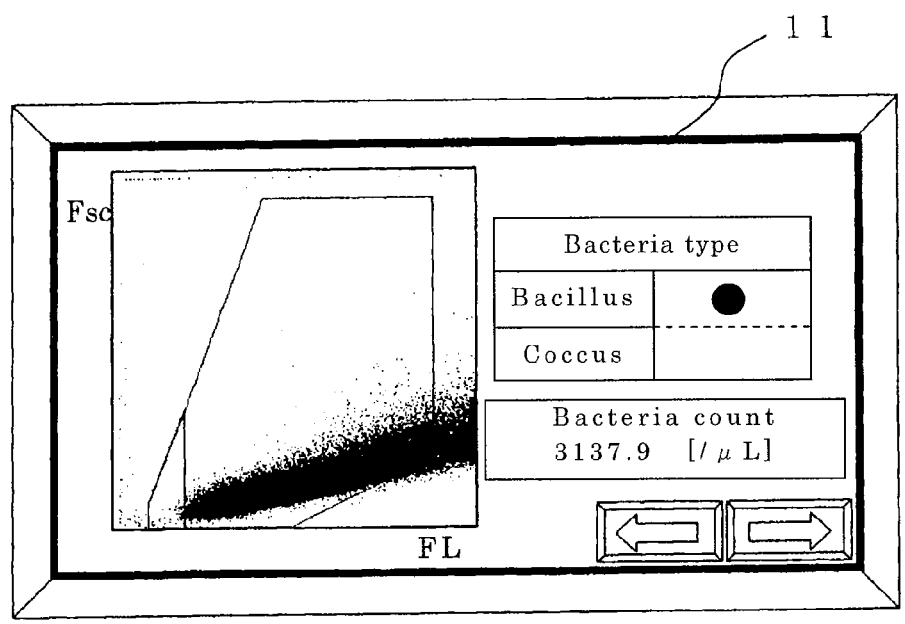
FIG. 10 shows an example of a screen displayed by an automated bacteria measuring apparatus embodying features of the present invention.
Figure 11:
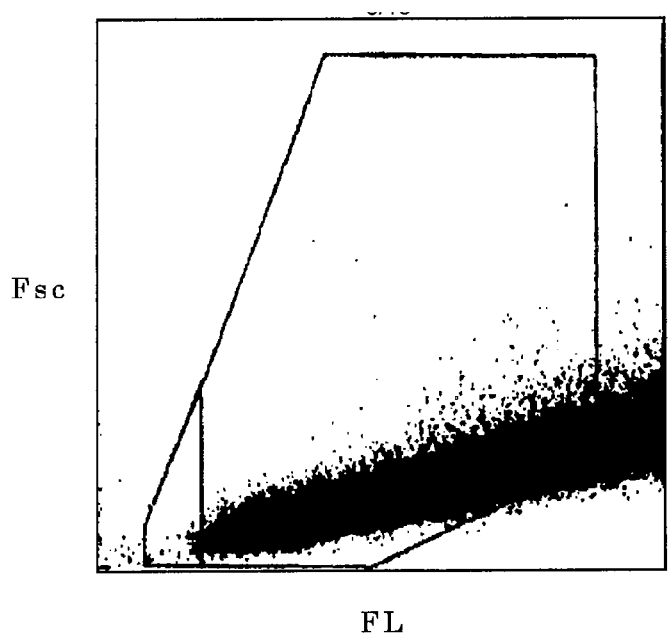
FIG. 11 shows an example of a scattergram prepared by an automated bacteria measuring apparatus embodying features of the present invention.
Figure 12:
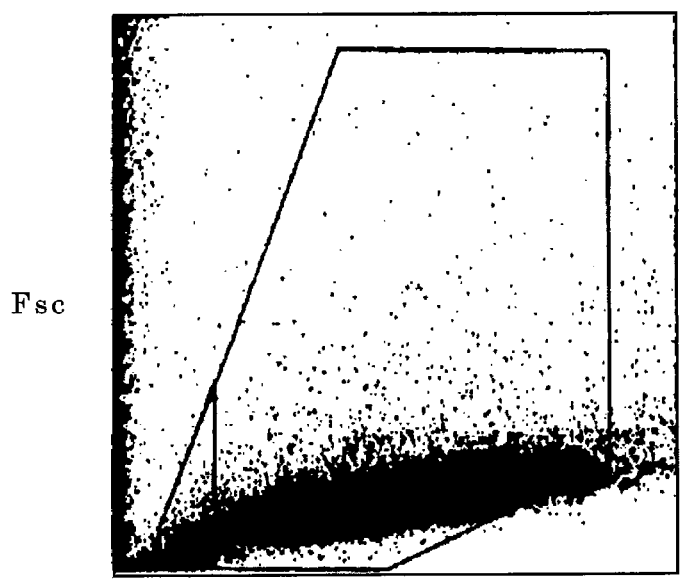
FIG. 12 shows an example of a scattergram prepared by an automated bacteria measuring apparatus embodying features of the present invention.
Figure 13:
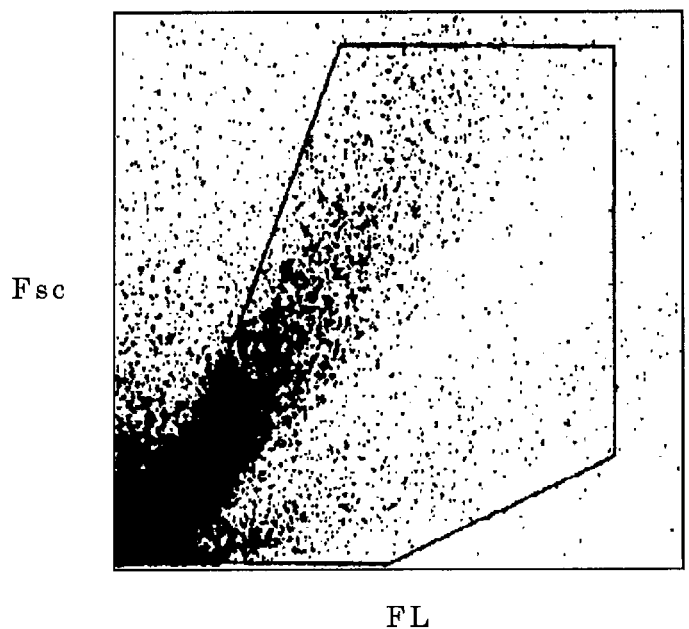
FIG. 13 shows an example of a scattergram prepared by an automated bacteria measuring apparatus embodying features of the present invention.
Figure 14:
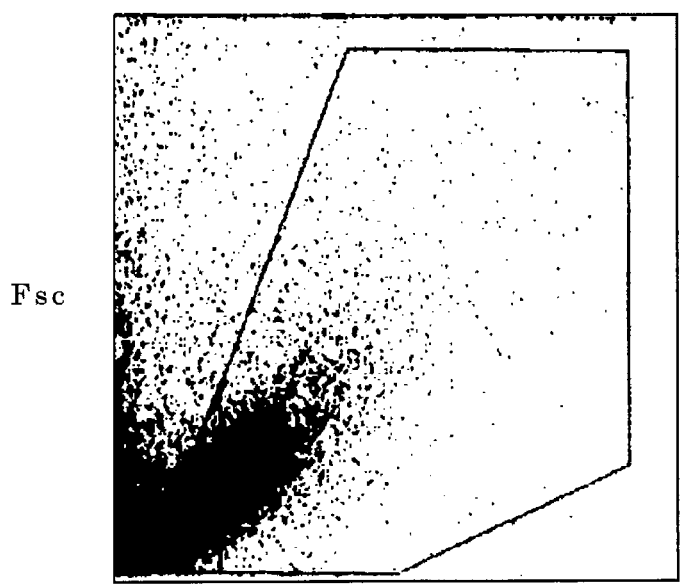
FIG. 14 shows an example of a scattergram prepared by an automated bacteria measuring apparatus embodying features of the present invention.

The result of the determination by the determining unit 144 is combined with the scattergram created in S2 and the bacteria count calculated in S3 and output to the output part (e.g. the liquid crystal touch panel 11) (S9). An example of the screen output to liquid crystal touch panel 11 is shown in FIG. 10. The scattergram, bacteria determination result, and bacteria count are displayed. In the spaces indicating the determination result for the type of bacteria, a mark is displayed in the [Bacillus] category among the [Bacillus] and [Coccus] categories to indicate that the determination result is *bacillus*.

Specimen Measurement Result Examples

The measurement of a specimen using the automated bacteria measuring apparatus 1 described above and the bacteria type determination results are described below.

Specimens

Specimens (a) through (g) described below were used.
(a) Human urine containing *E. aerogenes* (*bacillus*).
(b) Human urine containing *E. coli* (*bacillus*).
(c) Human urine containing *S. aureus* (*coccus*).
(d) Human urine containing *S. epidermis* (*coccus*).
(e) Heart infusion broth mixed with *E. coli* (*bacillus*) (bacteria count approximately $6 \times 10^5$/mL.
(f) Heart infusion broth mixed with *P. aeruginosa* (small type *bacillus*) (bacteria count approximately $6 \times 10^5$/mL).
(g) Heart infusion broth mixed with *S. aureus* (*coccus*) (bacteria count approximately $6 \times 10^5$/mL).

Assay Reagents

The specimens were processed using the dilution fluids and staining fluids listed below as reagents in preparing assay samples.

Dilution Fluids

| | |
|---|---|
| Citric acid | 100 mM |
| Sodium sulfate | 90 mM |
| Amidosulfuric acid | 100 mM |
| NaOH | enough to attain pH 2.5 |
| Tetra decyltrimethylammoniun bromide | 1 g |
| Purified water | 1 liter |

Staining Fluids

| | |
|---|---|
| Pigment having the structural formula below | 40 mg |

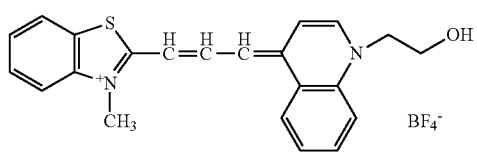

| | |
|---|---|
| Ethylene glycol | 1 liter |

The two-dimensional scattergrams obtained from the measurement results of specimens (a), (b), (c), and (d) are shown in FIGS. 11, 12, 13, and 14, respectively. In all cases, FL is plotted on the X axis (horizontal axis), and Fsc is plotted on the Y axis (vertical axis). The values of P calculated from the two-dimensional scattergrams in FIGS. 11 through 14, and the bacteria type determination results based on the flow charts are shown in Table 1.

TABLE 1

| Specimen | Bacteria type | P value | Determination result |
|---|---|---|---|
| (a) | *E. aerogenes* (*bacillus*) | 0.27 | Bacillus |
| (b) | *E. coli* (*bacillus*) | 0.23 | Bacillus |
| (c) | *S. aureus* (*coccus*) | 0.83 | Coccus |
| (d) | *S. epidermidis* (*coccus*) | 0.77 | Coccus |

As shown in Table 1, the P values calculated from the *bacillus*-containing specimens are smaller than the P values calculated from the *coccus*-containing specimens. Furthermore, the bacteria type determination results match the actual bacteria types based on the result of the comparisons of the P value obtained from each specimen and the predetermined value A (in this case A=0.68).

Figure 15:
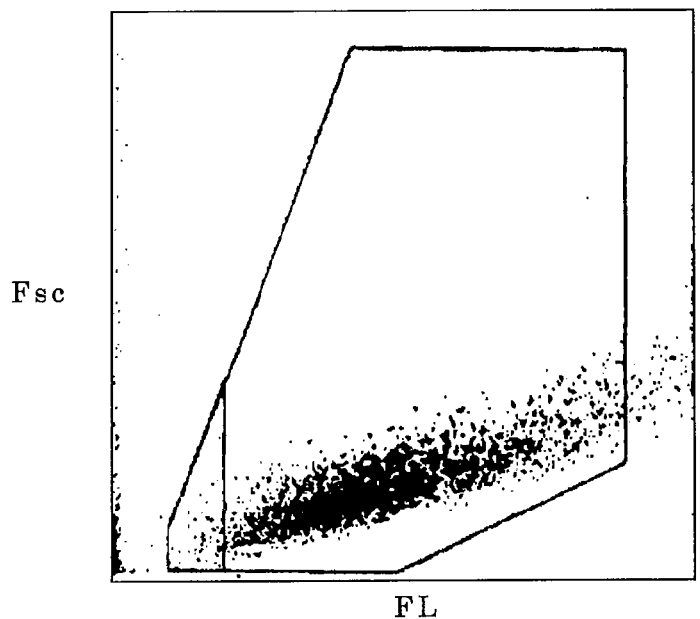
FIG. 15 shows an example of a scattergram prepared by an automated bacteria measuring apparatus embodying features of the present invention.
Figure 16:
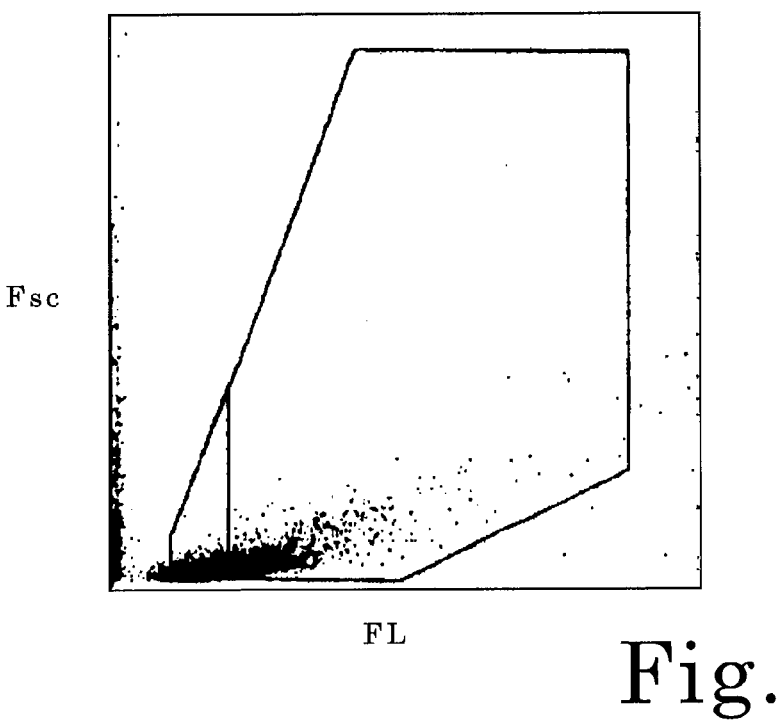
FIG. 16 shows an example of a scattergram prepared by an automated bacteria measuring apparatus embodying features of the present invention.
Figure 17:
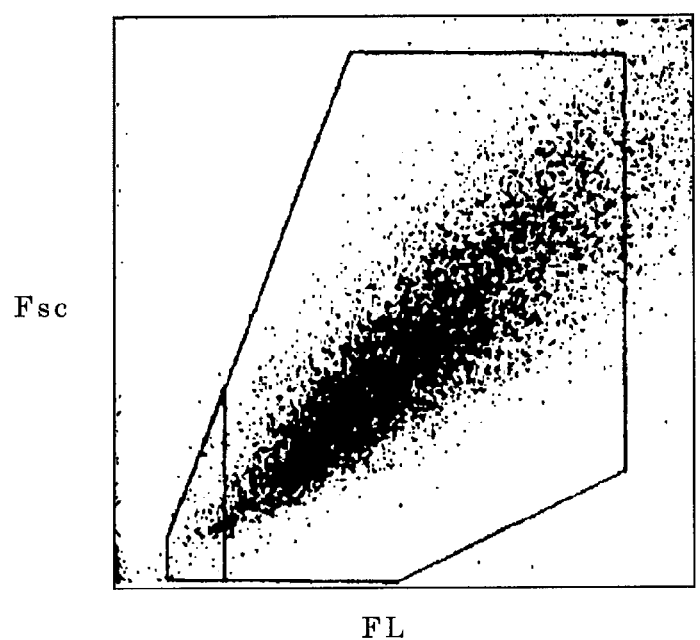
FIG. 17 shows an example of a scattergram prepared by an automated bacteria measuring apparatus embodying features of the present invention.

The two-dimensional scattergrams obtained from the measurement results of specimens (e), (f), and (g) are shown in FIGS. 15, 16, and 17, respectively. In all cases, FL is plotted on the X axis (horizontal axis), and Fsc is plotted on the Y axis (vertical axis). The values of P calculated from the two-dimensional scattergrams in FIGS. 15 through 17, and the bacteria type determination results based on the flow charts are shown in Table 2.

TABLE 2

| Specimen | Bacteria type | P value | Determination result |
|---|---|---|---|
| (e) | E. coli (bacillus) | 0.35 | Bacillus |
| (f) | E. aeruginosa (bacillus) | 0.21 | Bacillus |
| (g) | S. aureus (coccus) | 0.74 | Coccus |

As shown in Table 2, the P values calculated from the *bacillus*-containing specimens are smaller than the P values calculated from the *coccus*-containing specimens. Furthermore, the bacteria type determination results match the actual bacteria types based on the result of the comparisons of the P value obtained from each specimen and the predetermined value A (in this case A=0.68). When the large-type *bacillus E. coli* and the small-type *bacillus P. aeruginosa* are compared, the *P. aeruginosa* often appears at a position of lower value for Fsc in the two-dimensional scattergram, so that a difference arises in the state of distribution. However, both *E. coli* and *P. aeruginosa* may be accurately determined by the bacteria type determination based on the P value.

Determination Accuracy

Specimens of human urine which were bacteria typed by the plate agar culture method were measured using the automated bacteria measuring apparatus 1, and the bacteria typing determination accuracy is shown in Table 3.

TABLE 3

|  | *Bacillus*-containing specimens | *Coccus*-containing specimens | Total |
|---|---|---|---|
| Number of specimens | 53 | 26 | 79 |
| Number of matches | 47 | 21 | 68 |
| Accuracy (%) | 88.7 | 80.1 | 86.1 |

As shown in Table 3, 47 matches (accuracy 88.7%) were obtained among the *bacillus*-containing specimens, and 21 matches (accuracy 80.1%) were obtained among the *coccus*-containing specimens. Furthermore, there were 68 matches (accuracy 86.1%) among a total of 79 *bacillus*-containing specimens and *coccus*-containing specimens. Accordingly, the bacteria measuring apparatus of the present embodiment has a high determination accuracy greater than 80%.

Figure 6:
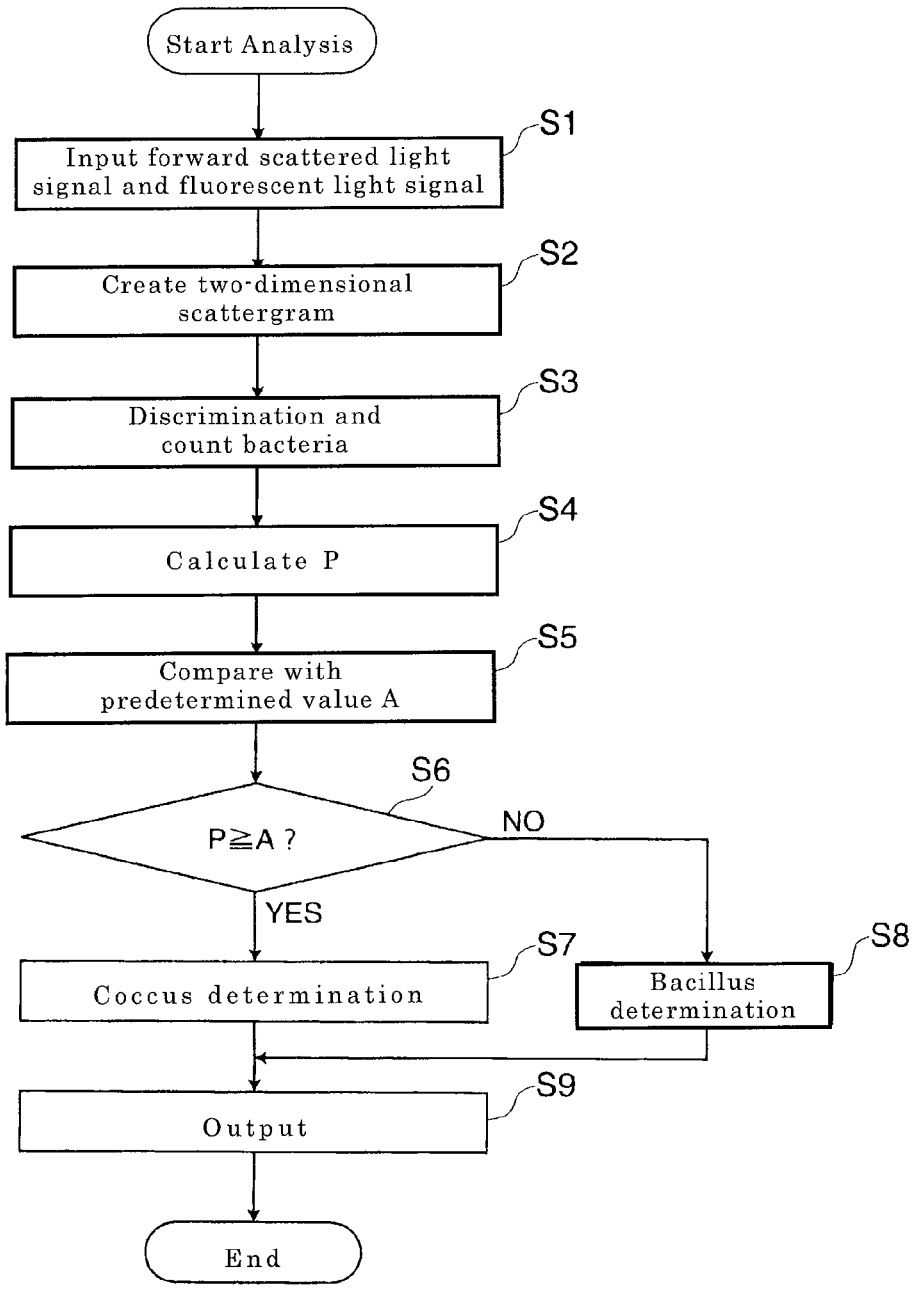
FIG. 6 is a flow chart showing the operation of an automated bacteria measuring apparatus embodying features of the present invention.
Figure 18:
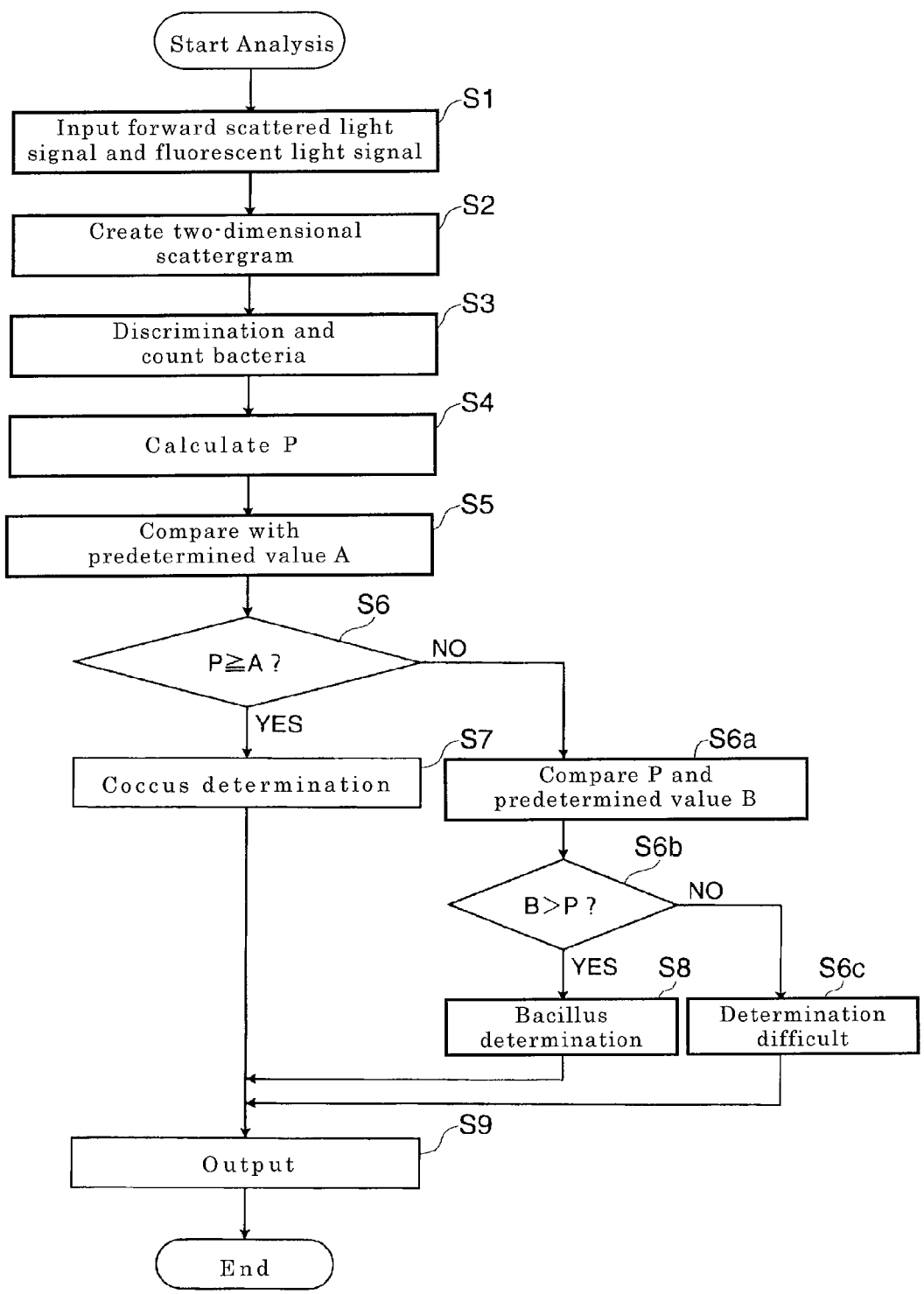
FIG. 18 is a flow chart of the operation of an automated bacteria measuring apparatus embodying features of the present invention.

FIG. 18 shows a modification of the sequence of the flow chart shown in FIG. 6. This example only modifies the sequence when P<A in S6, and is otherwise identical to FIG. 6.

In the flow chart of FIG. 18, the determination unit 144 compares the parameter P and a predetermined value B, which is less than A (e.g., B=0.60) when P<A (S6a). When P<B (S6b), the particles contained in the specimens are determined to be *bacillus* (S8), and when A>P≥B, determination is deemed difficult (S6b and S6c).

Figure 19:
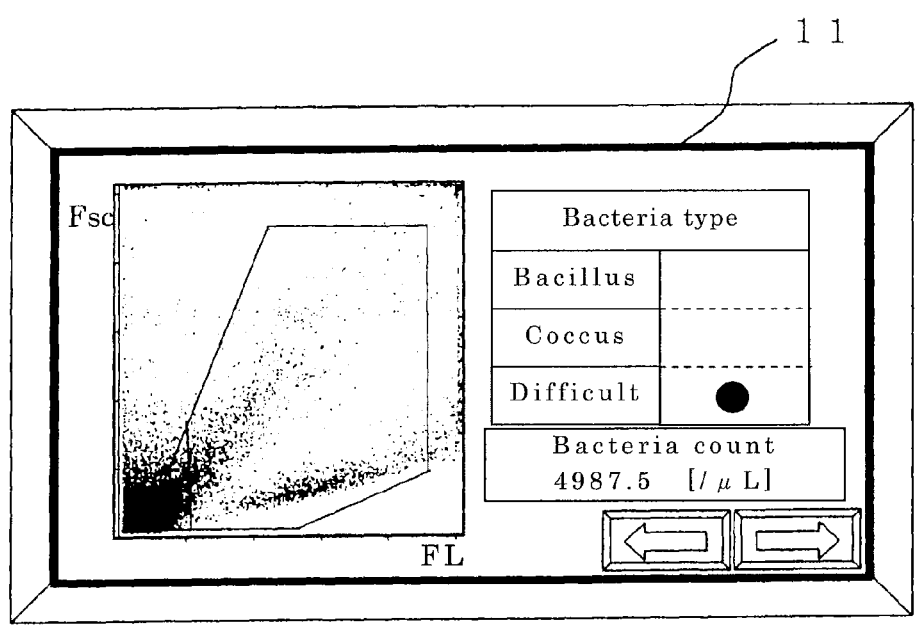
FIG. 19 shows an example of a screen displayed by an automated bacteria measuring apparatus embodying features of the present invention.

Screens corresponding to these determination results are output to the output part (e.g. the liquid crystal touch panel 11) (S9). Furthermore, the scattergram created in S2, and the bacteria count calculated in S3 are combined and output to the liquid crystal touch panel 11. An example of the screen output on the liquid crystal touch panel 11 is shown in FIG. 19. The two-dimensional scattergram, bacteria typing determination result, and bacteria count are displayed. In the spaces indicating the determination result for the type of bacteria, a mark is displayed in the [Determination Difficult] category among the [*Bacillus*], [*Coccus*], and [Determination Difficult] categories to indicate that the bacteria typing determination result for this specimen is difficult.

When A>P≥B in S6b of the flow chart in FIG. 18, and determination is difficult, an indication that determination is difficult is output as shown in FIG. 19 without determining whether the bacteria type is *bacillus* or *coccus*. However, the presence of bacteria whether *bacillus* or *coccus* may be suggested, or the possibility of the presence of bacteria may be indicated without suggesting the type.

Furthermore, when outputting the bacteria typing determination result, the degree of reliability of the determination result may also be output. For example, when bacteria in a specimen is determined to be either *bacillus* or *coccus*, the degree of dissociation of the calculated P value and the predetermined value A may be calculated and output, as in the flow chart of FIG. 6. The larger the degree of dissociation, the greater the reliability of the determination result. When either [*Bacillus*], [*Coccus*], or [Determination Difficult] is determined as in the flow chart of FIG. 18, when *coccus* is determined (P>A), the degree of dissociation between the P value and the predetermined value A is calculated. The larger the degree of dissociation, the higher the reliability of a result determining the bacteria is *coccus*. When *bacillus* is determined (P<B), the degree of dissociation between the P value and the predetermined value B is calculated. The greater the degree of dissociation, the higher the reliability of the result determining the bacteria is *bacillus*.

Although the present invention has been described above in terms of examples of presently preferred embodiments, the present invention is not limited to these examples. The present invention easily determines whether bacteria in a specimen is *bacillus* or *coccus* from the distribution of a scattergram created by bacteria size information and fluorescent light information. Since bacteria cultures are unnecessary in the present invention, it is possible to determine the bacteria type extremely quickly and efficiently.

The foregoing detailed description has been provided by way of explanation and illustration, and is not intended to limit the scope of the appended claims. Many variations in the presently preferred embodiments illustrated herein will be obvious to one of ordinary skill in the art, and remain within the scope of the appended claims and their equivalents.

The invention claimed is:
1. A urine measuring apparatus comprising:
a sampling device configured to sample a urine specimen comprising fluorescently stained bacteria;
a first detector configured to detect size information from each of the bacteria in the urine specimen;

a second detector configured to detect fluorescence information expressing an intensity of fluorescent light emitted from each of the bacteria in the urine specimen;

a processor;

a memory coupled to the processor including programs executable by the processor to:

create a scattergram of data from the size information and the fluorescence information obtained from the bacteria and determine a slope of a distribution of the data in the scattergram; and determine whether the bacteria in the urine specimen are *bacillus* or *coccus* based on the slope of the distribution.

2. The apparatus of claim 1, wherein the processor further executes programs to determine a variance of the distribution of the bacteria in the scattergram, wherein determining the slope of the distribution is based on the variance of the distribution.

3. The apparatus of claim 1, wherein the first detector is configured to detect forward scattered light obtained from the bacteria.

4. The apparatus of claim 1, further comprising:

a flow cell configured to flow the urine specimen comprising the fluorescently stained bacteria; and a laser light source configured to irradiate the urine specimen within the flow cell;

wherein the first detector detects scattered light emitted from the bacteria in the urine specimen; and wherein the second detector detects the fluorescent light emitted from the bacteria in the urine specimen.

5. The apparatus of claim 1, wherein the first detector comprises:

a member having a pore for passing the bacteria; and first and second electrodes, wherein the first detector is further configured to detect electrical resistance between the first and the second electrodes, which is generated by passage of the bacteria through the pore.

6. The apparatus of claim 1, further comprising:

a specimen holding part configured to hold the urine specimen;

a reagent holding part configured to hold fluorescent dye reagent; and a mixing part configured to mix the urine specimen and the fluorescent dye reagent to fluorescently stain the bacteria in the urine specimen.

7. The apparatus of claim 1, further comprising a display configured to display a result determined by the processor.

8. The apparatus of claim 1, wherein the processor further executes programs to exhibit the scattergram on a display.

9. The apparatus of claim 8, wherein the processor further executes programs to cause the display to exhibit the scattergram together with identification of the *bacillus* or *coccus* bacteria.

10. The apparatus of claim 1, wherein the processor further executes programs to count the bacteria based on the size information and the fluorescence information obtained from the bacteria, and to cause a display to exhibit the scattergram together with a result of counting the bacteria.

11. The apparatus of claim 1, wherein the processor further executes programs to compare the slope with first and second predetermined values stored in the memory and to exhibit a warning on a display when a value of the slope is between the first and second predetermined values indicating that it is difficult to determine the *bacillus* or *coccus* bacteria.

12. The apparatus of claim 1, wherein the processor further executes programs to cause a display to exhibit a degree of reliability for the *bacillus* or *coccus* bacteria as determined by the processor.

13. A urine measuring apparatus comprising:

a sample preparing device configured to prepare a measurement sample from a urine specimen and a fluorescent dye reagent that stains bacteria included in the urine specimen;

a detection device configured to detect size information from each of the bacteria in the measurement sample and to detect fluorescence information expressing an intensity of fluorescent light emitted from each of the bacteria in the measurement sample; and a processor and a memory coupled to the processor, the memory including programs executable by the processor to:

create a scattergram by using the size information and the fluorescence information obtained from the bacteria and determine a slope of bacteria distribution data in the scattergram; and determine whether the bacteria in the urine specimen are *bacillus* or *coccus* based on the slope of the bacteria distribution data.

14. The apparatus of claim 13, wherein the processor further executes programs to determine the slope of the bacteria distribution data based on a variance of the distribution of the bacteria distribution data in the scattergram.

15. The apparatus of claim 13, further comprising a display, wherein the processor further executes programs to cause the display to exhibit the scattergram together with the *bacillus* or *coccus* bacteria.

* * * * *